United States Patent
Koob

(10) Patent No.: US 10,335,433 B2
(45) Date of Patent: Jul. 2, 2019

(54) NDGA POLYMERS AND METAL COMPLEXES THEREOF

(71) Applicant: MiMedx Group, Inc., Marietta, GA (US)

(72) Inventor: Thomas J. Koob, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 13/860,473

(22) Filed: Apr. 10, 2013

(65) Prior Publication Data
US 2014/0308233 A1    Oct. 16, 2014

(51) Int. Cl.
| | |
|---|---|
| A61K 47/48 | (2006.01) |
| A61K 33/34 | (2006.01) |
| C08K 3/015 | (2018.01) |
| A61K 33/24 | (2019.01) |
| A61K 33/26 | (2006.01) |
| A61L 27/54 | (2006.01) |
| A61L 31/16 | (2006.01) |
| A01N 59/16 | (2006.01) |
| A01N 59/20 | (2006.01) |
| C08G 65/38 | (2006.01) |
| C08G 65/44 | (2006.01) |
| A61K 47/58 | (2017.01) |

(52) U.S. Cl.
CPC .............. *A61K 33/34* (2013.01); *A01N 59/16* (2013.01); *A01N 59/20* (2013.01); *A61K 33/24* (2013.01); *A61K 33/26* (2013.01); *A61K 47/58* (2017.08); *A61L 27/54* (2013.01); *A61L 31/16* (2013.01); *C08G 65/38* (2013.01); *C08G 65/44* (2013.01); *C08K 3/015* (2018.01); *A61L 2300/104* (2013.01)

(58) Field of Classification Search
CPC ................................................. A61K 47/48176
See application file for complete search history.

(56) References Cited

U.S. PATENT DOCUMENTS

| | | | |
|---|---|---|---|
| 4,703,108 A | 10/1987 | Silver et al. | |
| 4,847,049 A | 7/1989 | Yamamoto | |
| 4,874,049 A | 10/1989 | Kee et al. | |
| 5,118,867 A | 6/1992 | Bahrmann et al. | |
| 5,541,232 A | 7/1996 | Howell et al. | |
| RE35,748 E | 3/1998 | Luck et al. | |
| 5,807,581 A | 9/1998 | Rosenblatt et al. | |
| 6,129,757 A | 10/2000 | Weadock | |
| 6,166,184 A | 12/2000 | Hendriks et al. | |
| 6,503,244 B2 | 1/2003 | Hayman | |
| 6,565,960 B2 | 5/2003 | Koob et al. | |
| 6,716,895 B1 | 4/2004 | Terry | |
| 6,821,530 B2 | 11/2004 | Koob et al. | |
| 7,101,857 B2 | 9/2006 | Sung et al. | |
| 7,901,455 B2 | 3/2011 | Koob et al. | |
| 8,177,839 B2 | 5/2012 | Koob et al. | |
| 8,192,481 B2 | 6/2012 | King | |
| 8,367,148 B2 | 2/2013 | Greenhalgh et al. | |
| 2002/0019516 A1 | 2/2002 | Noff et al. | |
| 2002/0037940 A1* | 3/2002 | Koob et al. | 521/55 |
| 2003/0187515 A1 | 10/2003 | Hariri et al. | |
| 2003/0204023 A1 | 10/2003 | Koob et al. | |
| 2004/0048796 A1 | 3/2004 | Hariri et al. | |
| 2005/0142161 A1 | 6/2005 | Freeman et al. | |
| 2006/0141025 A1* | 6/2006 | Huang | A61K 9/0019 424/451 |
| 2007/0160573 A1 | 7/2007 | Gengrinovitch | |
| 2008/0020012 A1* | 1/2008 | Ju | A61L 27/34 424/423 |
| 2008/0046095 A1 | 2/2008 | Daniel | |
| 2008/0161917 A1 | 7/2008 | Koob et al. | |
| 2008/0181967 A1 | 7/2008 | Liu et al. | |
| 2008/0200992 A1 | 8/2008 | Koob et al. | |
| 2008/0233552 A1 | 9/2008 | Ma et al. | |
| 2009/0053290 A1 | 2/2009 | Sand et al. | |
| 2009/0092664 A1 | 4/2009 | Mumper et al. | |
| 2009/0216233 A1 | 8/2009 | Wiedrich et al. | |
| 2009/0287308 A1 | 11/2009 | Davis et al. | |
| 2010/0094318 A1 | 4/2010 | Li et al. | |
| 2010/0094404 A1 | 4/2010 | Greenhalgh et al. | |
| 2010/0104539 A1 | 4/2010 | Daniel et al. | |
| 2010/0272782 A1 | 10/2010 | Owens et al. | |
| 2010/0291182 A1 | 11/2010 | Palasis et al. | |
| 2010/0317677 A1 | 12/2010 | Hassel et al. | |
| 2011/0097379 A1 | 4/2011 | Yoo et al. | |
| 2011/0282447 A1 | 11/2011 | Niu et al. | |
| 2011/0282448 A1 | 11/2011 | Paulos et al. | |

(Continued)

FOREIGN PATENT DOCUMENTS

| | | |
|---|---|---|
| EP | 0 506 207 B1 | 9/1992 |
| EP | 2 434 048 A1 | 3/2012 |
| JP | 2008-513484 | 5/2008 |
| JP | 2012-072119 | 4/2012 |
| JP | 2016-530217 | 9/2016 |
| WO | WO-87/00062 A1 | 1/1987 |
| WO | WO-88/03805 A1 | 6/1988 |
| WO | WO-98/31404 | 7/1998 |
| WO | WO-01/00101 | 1/2001 |
| WO | WO-01/00151 A1 | 1/2001 |
| WO | WO-01/49696 A1 | 7/2001 |
| WO | WO-2007/083984 A1 | 7/2007 |
| WO | WO-2012/065937 A1 | 5/2012 |
| WO | WO-2012/069559 A1 | 5/2012 |
| WO | WO2012069558 A1 * | 5/2012 |
| WO | WO-2012/112417 A2 | 8/2012 |

OTHER PUBLICATIONS

Science Lab. "Cuprous chloride MSDS". Retrieved on Mar. 8, 2017. Retrieved from the internet <URL: http://www.sciencelab.com/msds.php?msdsId=9923602>.*

(Continued)

*Primary Examiner* — Doan T Phan
(74) *Attorney, Agent, or Firm* — Alston & Bird LLP

(57) ABSTRACT

Provided herein are NDGA polymers and metal complexes of such polymers, preferably those metal complexes of the polymers that are insoluble or substantially insoluble in an aqueous solvent, and processes for making the same.

11 Claims, No Drawings

(56) References Cited

U.S. PATENT DOCUMENTS

| | | |
|---|---|---|
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189586 A1 | 7/2012 | Harrell |
| 2012/0282348 A1 | 11/2012 | Yates et al. |
| 2013/0202676 A1 | 8/2013 | Koob et al. |
| 2014/0106447 A1 | 4/2014 | Brown et al. |
| 2014/0142025 A1 | 5/2014 | Koob |

OTHER PUBLICATIONS

ThermoFisher Scientific. "Separation Characteristics of Dialysis Membrane". Retrieved on Mar. 1, 2018. Retrieved from the internet. Publication date: Apr. 18, 2013.*
Koob and Hernandez, Material properties of polymerized NDGA-collagen composite fibers: Development of biologically based tendon constructs. Biomaterials, 23(1): 203-212, 2002.
U.S. Appl. No. 13/815,736, filed Mar. 15, 2013, Koob.
U.S. Appl. No. 13/815,775, filed Mar. 15, 2013, Koob.
U.S. Appl. No. 13/815,834, filed Mar. 15, 2013, Koob.
U.S. Appl. No. 13/903,878, filed May 28, 2013, Koob.
Borkow et al., "Reducing the risk of skin pathologies in diabetics by using copper impregnated socks", Medical Hypotheses, 2009, 1-4, doi:10.1016/j.mehy.2009.02.050.
Hannallah et al., "Cerebrospinal fluid leaks following cervical spine surgery," J. Bone Joint Surg. Am., 2008, 90(5):1101-1105.
Khan et al., "Postoperative management protocol for incidental dural tears during degenerative lumbar spine surgery: a review of 3,183 consecutive degenerative lumbar cases", Spine, 2006; 31(22):2609-2613.
Konishi et al., In vivo anti-tumor effect through the controlled release of cisplatin from biodegradable gelatin hydrogel,: J. Controlled Release, 2003, 92(3):301-313.
Koob et al., "Mechanical and thermal properties of novel polymerized NDGA-gelatin hydrogels", Biomaterials, 2003; 24(7):1285-1292.
Koob et al., "Material properties of polymerized NDGA-collagen composite fibers: Development of biologically based tendon constructs", Biomaterials, 23(1): 203-212, 2002.
Kostova, "Platinum Complexes as Anticancer Agents", Recent Patents on Anti-Cancer Drug Discovery, 2006; 1(1):1-22.
Lu et al., "Molecular mechanisms and clinical applications of nordihydroguaiaretic acid (NDGA) and its derivatives: An update," Med. Sci. Monit., 2010, 16(5):RA93-RA100.
Mayfield et al., "Watertight closure of spinal dura mater: Technical note", Journal of Neurosurgery, 1975; 43(5):639-640.
PCT International Search Report and Written Opinion dated Apr. 16, 2014 in PCT Patent Application No. PCT/US13/67622.
PCT International Search Report and Written Opinion dated Apr. 21, 2014 in PCT Patent Application No. PCT/US13/67623.
PCT International Search Report and Written Opinion dated Apr. 22, 2014 in PCT Patent Application No. PCT/US13/67618.
PCT International Search Report and Written Opinion dated Apr. 22, 2014 in PCT Patent Application No. PCT/US13/67620.
Kelly et al., "Disparate Effects of Similar Phenolic Phytochemicals as Inhibitors of Oxidative Damage to Cellular DNA", Mutation Res., vol. 485, pp. 309-318, (2001).
Moussy et al., "Transport characteristics of a novel local drug delivery system using nordihydroguaiaretic acid (NDGA)-polymerized collagen fibers," Biotechnology Progress, (2007), 23(4):990-994.
PCT International Search Report and Written Opinion dated Aug. 26, 2014 in PCT Patent Application No. PCT/US2014/033346.
International Preliminary Report on Patentability issued on PCT/US13/67620, dated Apr. 17, 2014.
PCT International Preliminary Report on Patentability dated Dec. 3, 2014 for PCT Patent Application No. PCT/US2013/067618.
PCT International Preliminary Report on Patentability dated Dec. 30, 2014 for PCT Patent Application No. PCT/US13/67622.
PCT International Preliminary Report on Patentability dated Nov. 10, 2014 for PCT Patent Application No. PCT/US2013/067623.
PCT International Search Report and Written Opinion dated Dec. 29, 2014 for PCT Patent Application PCT/US2014/053270.
Young Min Ju. A novel bio-stable 3D porous collagen scaffold for implantable biosensor; Ph.D. Dissertation 2008.
Young Min Ju. A novel bio-stable 30 porous collagen scaffold for implantable biosensor. Ph.D. Dissertation 2008.
Extended European Search Report dated Nov. 18, 2016 for European Application No. 14783309.9.

* cited by examiner

NDGA POLYMERS AND METAL COMPLEXES THEREOF

FIELD OF THE INVENTION

This invention relates to NDGA polymers and metal complexes of such polymers, preferably those metal complexes of the polymers that are insoluble or substantially insoluble in an aqueous solvent. This invention also relates to methods for preparing and using such polymers.

STATE OF THE ART

Nordihydroguaretic acid (NDGA) is a compound represented by the formula:

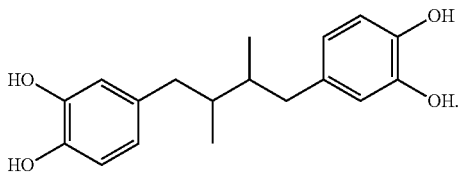 [SMILES: CC(Cc1ccc(O)c(O)c1)C(C)Cc1ccc(O)c(O)c1]

Koob, et al. have described methods of producing nordihydroguaiaretic acid (NDGA) polymerized and cross-linked to collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, each of which is incorporated in its entirety by reference.

SUMMARY OF THE INVENTION

Provided herein are NDGA polymers and metal complexes of such polymers, preferably those biologically compatible metal complexes of the polymers that are insoluble or substantially insoluble in an aqueous solvent, and processes for making the same. A variety of biologically compatible metals in a variety of oxidation states are useful for this invention, as will be apparent to the skilled artisan upon reading this disclosure. Preferably, the NDGA polymers described herein are either homopolymers or copolymers of NDGA with a biologically compatible monomer or mixture of such monomers.

In one aspect, this invention provides a metal-nordihydroguaretic acid (NDGA) polymer comprising metal atoms complexed at least in part to an NDGA polymer, wherein the NDGA polymer has a molecular weight of about 14,000 or more, and wherein the metal NDGA polymer is insoluble or substantially insoluble in an aqueous solvent. In one embodiment, the molecular weight of the polymer ranges from about 14,000 to about 500,000 and preferably from about 14,000 to about 100,000. The molecular weight of the polymer is independent of whether it is based on a number average or a weight average although a number average molecular weight is preferred.

In another aspect, the NDGA-polymer is prepared by a method which comprises oxidizing NDGA monomer, preferably in an aqueous medium, under conditions suitable to oxidize and polymerize NDGA. In one embodiment, the method further comprises separating the NDGA polymer from low molecular weight components including unreacted monomers and oligomers of molecular weight lower than 14,000 from the reaction mixture.

In one embodiment, the biologically compatible metal complexes of the polymers comprise ionic silver. In another embodiment, the ionic silver is chelated at least in part to a benzoquinone and/or a 1,2-dihydroxyphenyl moiety of the NDGA polymer although other suitable biologically compatible ions can be used such as ionic copper and platinum.

In one embodiment, the metal-NDGA polymer is provided in a powdered, micronized, or suspended (such as, in a aqueous solution) form.

In another aspect, this invention provides a process of precipitating a metal-nordihydroguaretic acid (NDGA) polymer, wherein the process comprises contacting a NDGA polymer with a biologically compatible metallic ions under conditions wherein at least a portion of said ions are chelated to the polymer.

In one embodiment, the contacting is performed in an aqueous solvent. In another embodiment, the metallic ion is ionic silver. In another embodiment, the metal is ionic silver which is chelated at least in part to a benzoquinone and/or a 1,2-dihydroxyphenyl moiety of the NDGA polymer. In another embodiment, the contacting is performed in vitro.

In various embodiments within the aspects and embodiments discussed above, the preferred biologically compatible metallic ion possesses antimicrobial, antifungal, and/or anticancer properties. Such metallic ions are well known to the skilled artisan. In one embodiment, the antimicrobial metal is silver, preferably silver (I). In another embodiment, the anti fungal metal is copper, preferably copper (II). In another embodiment, the anticancer metal is platinum, preferably, platinum (II).

DETAILED DESCRIPTION OF THE INVENTION

This invention relates to in part to NDGA polymers and metal complexes thereof. Before describing this invention in detail the following terms are defined.

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about".

As used herein, the singular forms "a", "an" and "the" are intended to include the plural forms as well, unless the context clearly indicates otherwise.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "aqueous solvent" means a liquid or a solution that includes water as a component, preferably as the single largest liquid component, and more preferably, as a major liquid component, that is >50% of the liquid component of the solvent. A non-limiting example of an aqueous solvent is phosphate buffered saline or PBS. Blood is another non-limiting example of an aqueous solvent.

The term "complexed" means a complexed metallic ion which is bound to an NDGA moiety or an oxidized or polymerized form thereof. The complexation typically involves ionic bonding. The metal atom can also be complexed via more than one point of attachment, and can thus be "chelated."

The term "substantially insoluble" in an solvent means that the metal-NDGA polymer precipitates from that solvent.

Polymerization of NDGA and Metal Complexation

NDGA polymerization typically proceeds in the presence of an oxidizing agent such as, by way of example, air, oxygen, ozone, and the like. In one preferred process, NDGA is dissolved in an aqueous alkali solution, such as NaOH or KOH solutions where the pH of the solution is above 7.5, and optionally an oxidizing agent is added or passed though (bubbled through) the solution or mixture. The NDGA polymer forms as a dark red mixture. Lower molecular weight oligomers and unreacted NDGA monomer is separated from the NDGA polymer by dialysis such that oligomers having a molecular weight of 14,000 or lower are removed from the NDGA polymers.

Without being bound by theory it is contemplated that, upon oxidation, the following illustrative and non-limiting radicals form:

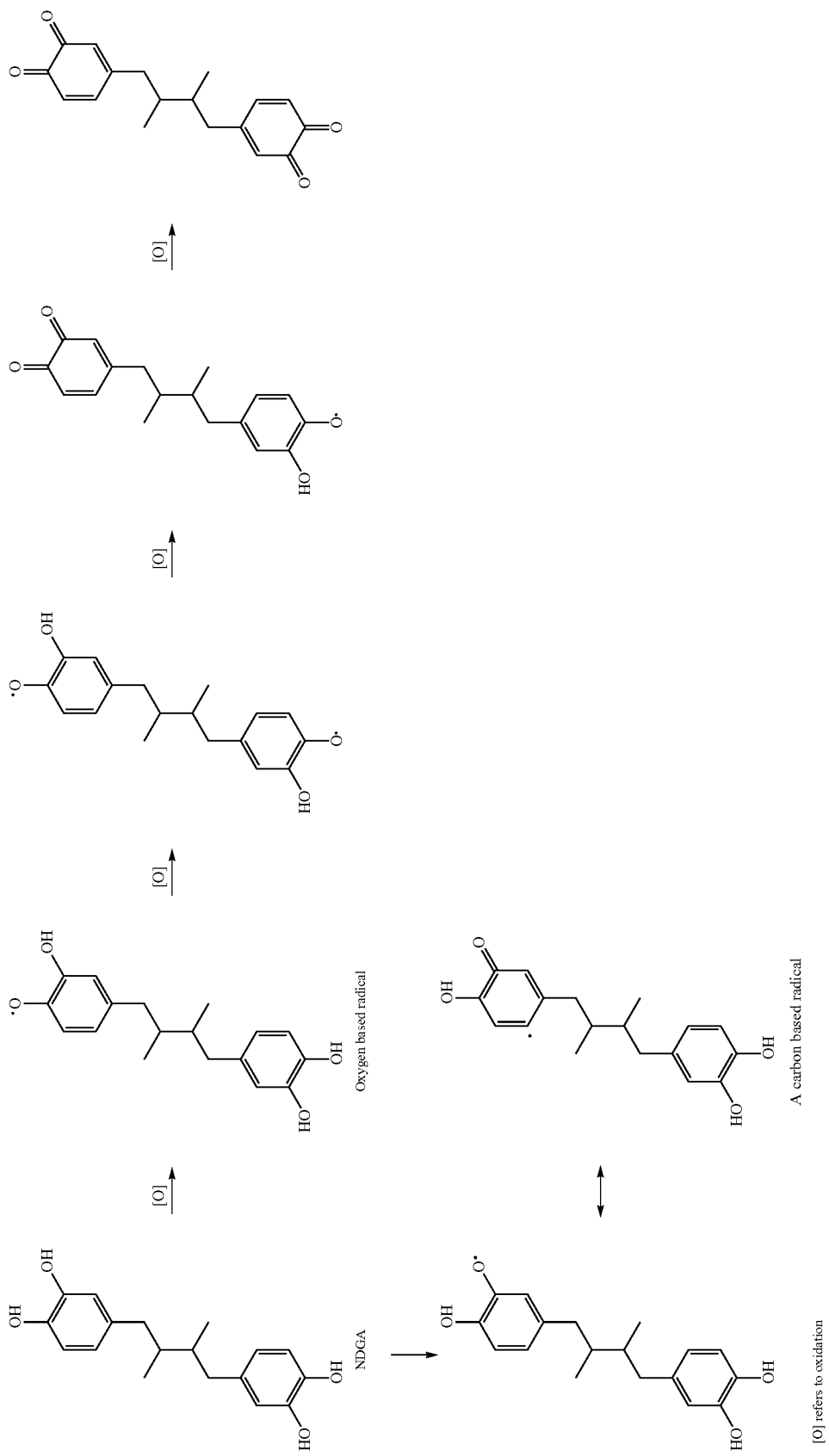

The oxygen or carbon based nucleophilic radicals react with the alpha, beta unsaturated electrophilic centers of the quinones to form NDGA polymers:

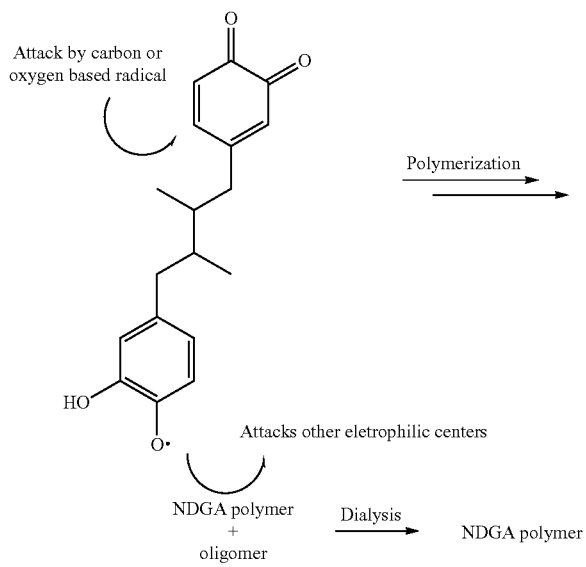

which are then separated as described above.

A mixture or a solution of the NDGA polymers formed as above are mixed with a suitable biologically compatible metallic ion under conditions to form the metal-NDGA polymer which precipitates from solution. The preferred biologically compatible metallic ion possesses antimicrobial, antifungal, and/or anticancer properties. Such metallic ions are well known to the skilled artisan. In one embodiment, the antimicrobial metal is silver, preferably silver (I). In another embodiment, the anti fungal metal is copper, preferably copper (II). In another embodiment, the anticancer metal is platinum, preferably, platinum (II). In one embodiment, the ionic platinum is cis-platin.

The metal-NDGA polymers can be used in a variety of applications. In one embodiment, the invention provides a method for treating cancer cells amenable to treatment with cis-platin, wherein the method comprises contacting said cancer cells with a sufficient amount of the complex of cis-platin with the NDGA polymer. In another embodiment, an antimicrobial method is provided, which comprises contacting a microbe with the complex of of silver with the NDGA polymer. In yet another embodiment, an antifungal method is provided, which comprises contacting fungi with the complex of of copper with the NDGA polymer.

EXAMPLE

Preparation of a Silver-NDGA-Bisquinone Polymer Complex of the Invention 100 mL of monomeric NDGA (30 mg/mL) was prepared by dissolving the NDGA in 0.4M NaOH solution. The NDGA solution was immediately added to 900 mL of 0.1 M $NaH_2PO_4$ having a pH of 7.0, and mixed thoroughly. The pH of the resulting mixture was then adjusted to about 10.0 to 11.0. The concentration of NDGA, NaOH, the molarity of NaOH and the molarity and pH of $NaH_2PO_4$ can be altered to obtain the reaction mixture having a final pH of about 10.0 to about 11.0. The reaction mixture was incubated with continuous mixing for 24 h at room temperature. The resulting solution was then dialyzed exhauatively against water in dialysis tubing with a MW cutoff of 12,000-14,000. NDGA is a low molecular weight di-catechol containing two ortho-catechols. The two catechols on NDGA undergo auto-oxidation at neutral or alkaline pH producing reactive quinones. Two quinones then couple via aryloxy free radical formation and oxidative coupling, forming bisquinone crosslinks at each end. The NDGA continues forming a large cross-linked bisquinone polymer network. In one embodiment, this polymer solution can directly be used to treat tissues before exposure to metallic ions. In another embodiment, a suitable amount of a silver(I) salt, such as silver acetate was added to the polymer solution causing the silver-NDGA bisquinone polymer to precipitate. The precipitate is separated by filtration and optionally vacuum dried and sterilized under appropriate conditions such as e-beam irradiation.

Preparation of Tissue/Biomaterial with Silver-NDGA-Bisquinone Polymer Complex of the Invention Dry tissues or other biomaterials are hydrated in a solution (such as an aqueous solution) of NDGA bisquinone polymer. The tissues/biomaterials are removed from the solution, blotted to remove excess solution, and then placed in a desired concentration of a silver(I) salt, such as silver acetate, in water. As the silver diffuses in to the tissue/biomaterial, the silver-NDGA polymer precipitates within the material thereby forming a depot of silver. The tissue/biomaterial is then dried and packaged.

In another embodiment, dry tissues or other biomaterials are placed in a solution of silver-NDGA bisquinone polymer for sufficient time to allow the polymer to diffuse in to the tissue, prior to drying and packaging.

Utility

The metal-NDGA polymers and their powdered, micronized, and such other forms are useful for delivering an antimicrobial, antifungal, anticancer metal, and such other therapeutically useful metals to a desired site containing the microbe, the fungus, or the cancer, or to a site that has a need for the metal. Because these metal-NDGA polymers are at least substantially insoluble in body fluids, the body fluids are contemplated to not carry them away from the desired site, thus enhancing therapy at the desired site and reducing unwanted side effects at unaffected normal tissue.

The invention claimed is:

1. A biologically compatible metal-nordihydroguaiaretic acid (NDGA) polymer complex, said complex comprising a metallic ion and a NDGA moiety, wherein said metallic ion is bound to the NDGA moiety of the polymer, wherein said complex is substantially insoluble in biological fluids; and wherein the complex is in a powdered form.

2. The complex of claim 1, wherein the metallic ion is selected from the group consisting of ionic silver, ionic copper and ionic platinum.

3. The complex of claim 2, wherein the metallic ion is ionic silver.

4. An antimicrobial method which comprises contacting a microbe with the complex of claim 3.

5. The complex of claim 2, wherein the metallic ion is ionic copper.

6. An antifungal method which comprises contacting fungi with the complex of claim 5.

7. The complex of claim 2, wherein the metallic ion is ionic platinum.

8. The complex of claim 7, wherein the ionic platinum is $Pt^{2+}$.

9. The complex of claim 8, wherein the ionic platinum is cis-platin.

10. A method for treating cancer amenable to treatment with cis-platin, said method comprises contacting said cancer with a sufficient amount of the complex of claim 9.

11. The complex of claim 1, wherein the NDGA polymer has a molecular weight of about 14,000 or more.

\* \* \* \* \*